United States Patent
Li et al.

(12) 
(10) Patent No.: US 6,291,174 B1
(45) Date of Patent: Sep. 18, 2001

(54) DNA MARKERS FOR PIG LITTER SIZE

(75) Inventors: Ning Li; Changxin Wu; Yaofeng Zhao, all of Beijing (CN)

(73) Assignee: Pig Improvement Company UK Limited, Oxfordshire (GB)

(*) Notice: Subject to any disclaimer, the term of this patent is extended or adjusted under 35 U.S.C. 154(b) by 0 days.

(21) Appl. No.: 09/329,796

(22) Filed: Jun. 10, 1999

Related U.S. Application Data

(60) Provisional application No. 60/088,963, filed on Jun. 10, 1998.

(51) Int. Cl.[7] .............................. C12Q 1/68; C12P 19/34; C07H 21/04
(52) U.S. Cl. .............................. 435/6; 435/91.2; 536/23.1
(58) Field of Search ....................... 435/6, 91.2; 536/23.1

(56) References Cited

U.S. PATENT DOCUMENTS

| | | | |
|---|---|---|---|
| 4,946,778 | 8/1990 | Ladner et al. | 435/69.6 |

FOREIGN PATENT DOCUMENTS

| | | |
|---|---|---|
| 0320308 | 12/1988 | (EP) . |
| 92018651 | 10/1992 | (WO) . |
| 96041892 | 12/1996 | (WO) . |

OTHER PUBLICATIONS

Li et al. Biology of Reproduction. Aug. 1997. vol. 56, Supp. p. 119, abstract #148.*
Rohrer et al. Mammilian Genome, 5, 315–317 (1994).*
Wang Yaochun, et al., "Effects of Different Dietary Anions and Cations on Blood Acid–Base Balance and Incidence of Tibial Dyschondroplasia of 21 Day–Old Broiler Chicks," (w/English Abstract), *Acta Veterinaria et Zootechnica Sinica,* vol. 30. pp. 211–216 (1999).
Jiao Shuxian, et al., "Serum Profiles of Five Reproductive Hormones During First Estrous Cycle in Fengjing and Landrace Gilts," (w/English Abstract), *Acta Veterinaria et Zootechnica Sinica,* vol. 23. pp. 202–206 (1992).
Danuta Kozbor, et al., "The Production of Monoclonal Antibodies from Human Lymphocytes," *Immunology Today,* vol. 4, No. 3, pp. 72–79, (1983).
Max Rothschild, et al., "The Estrogen Receptor Locus is Associated with a Major Gene Influencing Litter Size in Pigs," *Proc. Natl. Acad. Sci, USA,* vol. 93, pp. 201–205 (1996).
William D. Huse, et al., "Generation of a Large Combinatorial Library of the Immunoglobulin Repertoire in Phage Lambda," *Science,* vol. 246, pp. 1275–1281 (1989).
T. Wise, et al., "Differential Pituitary and Gonadal Function of Chinese Meishan and European White Composite Boars: Effects of Gonadotropin–Releasing Hormone Stimulation, Castration, and Steroidal Feedback," *Biology of Reproduction,* vol. 54, pp. 146–153 (1996).
T. Hirai, et al., "The Gene for the β Subunit of Procine FSH: Absence of Consensus Oestrogen–Responsive Element and Presences of Retroposons," *Journal of Molecular Endocrinology,* vol. 5, pp. 147–158, (1990).

\* cited by examiner

*Primary Examiner*—Jeffrey Fredman
*Assistant Examiner*—Juliet Einsmann
(74) *Attorney, Agent, or Firm*—Brobeck, Phleger & Harrison LLP

(57) ABSTRACT

Methods are provided for screening pigs to determine those more likely to produce larger litters. The screening method detects the presence of particular alleles in the genome, and in a preferred embodiment, the screening is performed by nucleic acid analysis. Specific primers as well as kits for carrying out the methods of the invention are also provided.

3 Claims, No Drawings

SEQUENCE LISTING

<160> NUMBER OF SEQ ID NOS: 4

<210> SEQ ID NO 1
<211> LENGTH: 291
<212> TYPE: DNA
<213> ORGANISM: Sus scrofa

-continued

```
<400> SEQUENCE: 1
ggagttcccc gtcgtggcgc agtggttaac gaatccgatt aggaaccatg aggttgcggg      60
ttcggtccct gcccttgctc agtgggttaa tgatccggcg ttgcatgagc tgtggtgtag     120
gttgcagacg aggctcggat ccccgcgttg ctgtggtttc tggcgtaggc gggtggctac     180
agttttgatt cgacccctag cctgggaacc tccatatgcc gcgggagcgc ccaaagaaat     240
ggcaaaagac gaaaaaaaaa aaaaaaaaa aaaaaaaaa aaaaaacgtt t                 291

<210> SEQ ID NO 2
<211> LENGTH: 1181
<212> TYPE: DNA
<213> ORGANISM: Sus scrofa

<400> SEQUENCE: 2
ttggagtttc catcgtgggc gcaatggtta acgaatcgac taggaaccaa gaggttgcgg      60
gttcgatccc tggccttgct cagtgggtta aggatccagc attgctgtga gctgtggtgt     120
aggttacaga cacagcttgg atcccacgtt gctgtggccc tggcataggg cgatggctac     180
agctctgatt agacccctag ccttggaaac tccatatgcc aagggagcag tccaagaaat     240 ggcaaaaga ccaaaaaaaa agttttctt tttaaataaa atgttttaaa atgataatga       300
agggacaaat atgatgatca caattacttg cttcagagta atcctttaag acagtcaatg     360
gcaatactct ataaatattg ctctgcttca aaacattata ttggagtttt gacccataat     420
atagttctac tttgacaaaa aaaaaaaaaa ttgaggagga gaataagaag aaacgttttg     480
gagttccccg tcgtggcgca gtggttaaac gaatccgatt aggaaccatg aggttgcggg     540
ttcggtccct gcccttgctc agtgggttaa tgatccggcg ttgcatgagc tgtggtgtag     600
gttgcagacg aggctcggat ccccgcgttg ctgtggtttc tggcgtaggc gggtggctac     660
agttttgatt cgacccctag cctgggaacc tccatatgcc gcggggagcg cccaaagaaa     720
tggcaaaaga cagaaaaaaa aaaaaaaaaa aaaaaaaaa aaaagaaacg tttgttcaag     780
aaacaaagaa ttaaagaaaa ggaaaaggaa ggaaaaacca ctataggagt aaaatgtgac     840
tggagaggat gaatagacca gttattcaag gtttggtcaa cttacattac gaatgtaatt     900
ctttggtttt ttcagttttt tacaggcctt aattgtttgg tttccacccc aagatgaagt     960
cgctgcagtt ttgcttccta ttctgttgct ggaaagccat ctgctgcaat agctgtgagc    1020
tgaccaacat caccatcaca gtggagaaag aggagtgtaa cttctgcata agcatcaaca    1080
ccacgtggtg tgctggctat tgctacaccc gggtaggttc tttgctttgc tagaagtgag    1140
ggtgctgaag gtctgtaaaa ggcgggcttt actaattccc c                        1181

<210> SEQ ID NO 3
<211> LENGTH: 19
<212> TYPE: DNA
<213> ORGANISM: Sus scrofa

<400> SEQUENCE: 3
cctttaagac agtcaatgc                                                    19

<210> SEQ ID NO 4
<211> LENGTH: 20
<212> TYPE: DNA
```

-continued

```
<213> ORGANISM: Sus scrofa

<400> SEQUENCE: 4
actggtctat tcatcctctc                                              20
```

DNA MARKERS FOR PIG LITTER SIZE

This application is related to U.S. Provisional Application No. 60/088,963 filed on Jun. 10, 1998.

The present invention relates to methods of screening pigs to determine the presence or absence of alleles of the Follicle-Stimulating hormone β subunit gene associated with increased litter size, to the use of such methods in predicting litter size in pigs and to kits for carrying out such methods.

Meat production and animal breeding efficiencies could be improved if it were possible to increase animal litter sizes. The same output of livestock could be derived from fewer parent animals, thus providing decreased production costs. In addition, animal breeding organizations would benefit from the potential to screen more offspring for those with improved genetics. However, litter size is very difficult to select for conventionally, as it is limited to one sex and is heavily influenced by non-genetic factors (heritability, a measure of the fraction of the phenotypic variation that is due to genetic differences, is approximately 0.1 for litter size in the pig).

One approach to improving litter size might be to introduce beneficial genes into production lines from breeds which have significantly higher litter sizes. However, quantitative genetics suggests that complex traits such as litter size are controlled by a large number of genes each having a small effect on the trait. If this is true, genetic progress through selection of complex traits is likely to be very slow. An alternative view is that, although many genes are involved in complex traits, a few of the genes involved (major genes) have large effects on the trait. If this alternative view is true, then genetic progress of such traits could be rapid, provided that it is possible to identify and select for beneficial alleles of relevant major genes. Since the advent of genome mapping, it has become possible to identify genes affecting quantitative traits (quantitative trait loci, QTL) by looking for associations between the trait and molecular markers distributed evenly across the genome of animals for which maps are available. Importantly, for selection purposes, the heritability of such marker phenotypes is 1.0.

The Chinese Meishan breed of pig is known to produce about 4 extra piglets per litter than the most prolific European breeds. Genes for prolificacy (litter size) from this breed would be of great value in programmes aimed at increasing the litter size of commercial Western pig breeds. Indeed a genetic marker associated with the oestrogen receptor gene (ESR) of the Meishan has been shown to have beneficial effects on litter size and is described in WO92/18651. In addition, in WO96/41892 there were disclosed methods for testing pigs for alleles of the Osteopontin gene associated with larger litter size in pigs.

We have now characterised a polymorphism in the porcine FSH β-subunit gene and have established that the polymorphism is associated with litter size in pigs.

Mammalian follicle stimulating hormone (FSH) is a glycoprotein composed of two subunits, an α-subunit (which is also common to other glycoprotein hormones such as LH and TSH) and a unique β-subunit. The sequence of the B-subunit was reported by Hirai, et al., *J. Mol. Endocrinol.,* 5:147–158 (1990) and is available under Genbank accession No. D00621, Locus "PIGFSHBS". In general, FSH is secreted from the anterior pituitary under the stimulation of GnRH and reaches target tissue in the gonads via the blood. It interacts with its receptor on granular cells, promoting the maturation and differentiation of ovarian follicles. FSH and LH play an important role in the development of the oocyte before fertilization.

The present inventors have determined that there is a mutation in the FSH β-subunit gene in certain pig breeds which results from the insertion of a retroposon, which contains a complete promoter for RNA polymerase II as well as other possible transcription regions. Litter sizes in pigs carrying the mutation are significantly different from those of pigs lacking the mutation.

Thus, in a first aspect the present invention provides a method for screening pigs to determine those more likely to produce larger litters, and/or those less likely to produce larger litters, by determining whether the pigs carry the FSH β mutation. In one mode this method comprises the steps:

(i) obtaining a sample of pig nucleic acid; and (ii) analysing the nucleic acid obtained in (i) to determine which FSH β-subunit allele(s) is/are present.

Suitably, the nucleic acid is a sample of pig nucleic acid and step (ii), namely the determination of FSH β-subunit alleles, is carried out by looking for particular DNA markers linked either directly or indirectly to the FSH β-subunit gene.

Association between genetic markers and genes responsible for a particular trait can be disrupted by genetic recombination. Thus, the closer the physical distance between the marker and the gene in question, the less likely it is that recombination will separate them. It is also possible to establish linkage between specific alleles of alternative DNA markers and alleles of DNA markers known to be associated with a particular gene (e.g. the FSH β-subunit gene discussed herein), which have previously been shown to be associated with a particular trait. In a further embodiment of the invention a number of such markers are used. For example, pairs of markers might be utilised to bracket the major gene to reduce any possible effects of recombination.

As discussed above, the mutation described herein consists of the insertion of a retroposon. The presence of the retroposon is associated with smaller litter size. The retroposon is located at the border of Intron I and Exon II of the FSH β-subunit gene, at 809 bp (with the transcription start site labelled 0), and is 292 bp in length This retroposon has the sequence:

```
GGAGTTCCCCGTCGTGGCGCAGTGGTTAACGAATCCGATTAGGAACC          (SEQ ID NO:1)

ATGAGGTTGCGGGTTCGGTCCCTGCCCTTGCTCAGTGGGTTAATGATC

CGGCGTTGCATGAGCTGTGGTGTAGGTTGCAGACGAGGCTCGGATCCC

CGCGTTGCTGTGGTTTCTGGCGTAGGCGGGTGGCTACAGTTTTGATTC

GACCCCTAGCCTGGGAACCTCCATATGCCGCGGGAGCGCCCAAAGAA

ATGGCAAAAGACGAAAAAAAAAAAAAAAAAAAAAAAAAAAAAAAAA

AAACGTTT
```

The sequence of the retroposon together with a portion of the 5' and 3' flanking sequence is as follows, where upper case represents the retroposon sequence and lower case represents flanking sequence:

5'ttggagtttccatcgtgggcgcaatggttaacgaatcgactaggaaccaagaggttgcgggttcgatccctggcctt     (SEQ ID NO:2)

gctcagtgggttaaggatccagcattgctgtgagctgtggtgtaggttacagacacagcttggatcccacgttgctgtg gccctggcatagggcgatggctacagctctgattagacccctagccttggaaactccatatgccaagggagcagtcc aagaaatggcaaaaagaccaaaaaaaaagttttctttttaaataaaatgttttaaaatgataatgaagggacaaatatgat gatcacaattacttgcttcagagtaatcctttaagacagtcaatggcaatactctataaatattgctctgcttcaaaacattat attggagttttgacccataatatagttctactttgacaaaaaaaaaaaaaattgaggaggagaataagaagaaacgtttt

GGAGTTCCCCGTCGTGGCGCAGTGGTTAAACGAATCCGATTAGGAAC

CATGAGGTTGCGGGTTCGGTCCCTGCCCTTGCTCAGTGGGTTAATGAT

CCGGCGTTGCATGAGCTGTGGTGTAGGTTGCAGACGAGGCTCGGATCC

CCGCGTTGCTGTGGTTTCTGGCGTAGGCGGGTGGCTACAGTTTTGATT

CGACCCCTAGCCTGGGAACCTCCATATGCCGCGGGGAGCGCCCAAAG

AAATGGCAAAAGACAGAAAAAAAAAAAAAAAAAAAAAAAAAAAAAA

AAGAAACGTTTgttcaagaaacaaagaattaaagaaaaggaaaaggaaggaaaaaccactataggagta aaatgtgactggagaggatgaatagaccagttattcaaggtttggtcaacttacattacgaatgtaattctttggtttttttca gttttttacaggccttaattgtttggtttccaccccaagatgaagtcgcgtgcagttttgcttcctattctgttgctggaaacc atctgctgcaatagctgtgagctgaccaacatcaccatcacagtggagaaagaggagtgtaacttctgcataagcatca acaccacgtggtgtgctggctattgctacacccgggtaggttctttgctttgctagaagtgagggtgctgaaggtctgta aaaggcgggctttactaattcccc-3'

Thus, in one embodiment of the first aspect of the invention, step (ii) consists of analysing the nucleic acid to determine the presence and/or absence of the retroposon. The skilled person will appreciate that this can be achieved using suitable probes, which may be labelled for instance, which would bind to at least a part of the retroposon sequence. Alternatively, PCR amplification of the nucleic acid can be carried out. Methods for amplification are well known in the art (see e.g., Innis et al., 1990, PCR Protocols, Academic Press, Inc., San Diego, Calif.; ligase chain reaction (see EP 320,308); use of Qβ replicase; cyclic probe reaction; or other methods known in the art, which references are hereby incorporated by reference).

In the present case, PCR amplification products of differing lengths are obtained, depending on whether or not the retroposon is present on one or both of the particular chromosome pair. Thus, the size of the PCR amplified DNA fragment is 516 bp if the retroposon is present in the DNA or is 224 bp if it is not. Thus, alleles of the FSH β-subunit gene can be characterised as A where the retroposon is present, and B where it is not. Thus, an AA homozygote will present two amplified bands of 516 bp, an AB heterozygote one of 516 bp and one of 224 bp and a BB homozygote two bands of 224 bp.

An example of a suitable pair of primers which can be used for the PCR amplification is:

forward:  5'CCTTTAAGACAGTCAATGC 3'   (SEQ ID NO:3);

and reverse:  5'ACTGGTCTATTCATCCTCTC 3'  (SEQ ID NO:4)

Of course, the skilled person will appreciate that other suitable primers can be designed with reference to the FSH β sequence, and more particularly, with reference to the above-noted retroposon and flanking sequences.

Other alternative methods for the determination will include analysis of transcription products, ie. mRNA analysis or translation products. Clearly the transcription products will be different if the retroposon is present. In addition, analysis of the FSH β-subunit itself will enable the skilled person to determine whether the retroposon is present. Suitably, in this embodiment antibodies specific for an epitope associated with the retroposon or its absence can be utilised in methods for detecting the presence or absence of the mutant protein. The antibodies used include but are not limited to polyclonal, monoclonal, chimeric, single chain, Fab fragments, and an Fab expression library.

Various procedures known in the art may be used for the production of polyclonal antibodies to FSH β, or derivative or analog. In particular, antibodies which recognize epitopes that are found only on FSH β containing the retroposon, or alternatively epitopes that only appear in the absence of the retroposon are contemplated. For the production of antibody, various host animals can be immunized by injection with the native FSH β, or a synthetic version, or derivative (e.g., fragment) thereof, including but not limited to rabbits, mice, rats, horses, goats, chickens, etc. Various adjuvants may be used to increase the immunological response, depending on the host species, and including but not limited to complete or incomplete Freund's adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum.

For preparation of monoclonal antibodies directed toward FSH β, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). (Each of the foregoing references in incorporated herein by reference.)

According to the invention, techniques described for the production of single chain antibodies (U.S. Pat. No. 4,946, 778, incorporated herein by reference) can be adapted to produce FSH β-specific single-chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for the protein features, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments One can detect FSH β containing the retroposon by any detection means known in the art, including immunoassay or immunohistochemistry detected by for example, a radiolabel or a stain. A particularly useful stain employs peroxidase, hydrogen peroxide and a chromogenic substance such as aminoethyl carbazole. The peroxidase (a well known enzyme available from many sources) can be coupled to an anti-FSH antibody or merely complexed via one or more antibodies to an antibody which specifically binds FSH containing the retroposon. Such techniques are well known in the art. Other chromogenic substances and enzymes may also be used. Radiolabeling of antibodies may also be used to detect antibody binding to sections.

The precise technique by which the presence of FSH containing the retroposon is detected in pigs is not critical to the invention. Biochemical or immunological techniques can be used, including immunohistochemistry. Solution assay methods, including colorimetric, chemiluminescent or fluorescent immunoassays such as ELISA, sandwich and competitive immunoassays, immuno-diffusion, radio immunoassay, immunoelectrophoresis, Western blot and other techniques, may be used to detect and quantitate FSH containing the retroposon in a pig sample.

FSH containing the retroposon can be quantitated in a biological fluid, such as serum, plasma, effusions, ascites, urine, cerebrospinal fluid, semen, breast aspirates and fluids of ovarian origin, using any protein detection means known in the art. Preferred methods employ immunological detection means. These include: radioimmunoassay, enzyme linked immunoadsorbent assay, complement fixation, nephelometric assay, immunodiffusion or immunoelectrophoretic assay and the like. Plasma is preferably anticoagulated before use, as is known in the art. Cellular elements and lipid may be removed from fluids, e.g., by centrifugation. For dilute fluids, such as urine, protein may be concentrated, e.g., by ultra-filtration or salting-out.

In another aspect, the present invention provides a method of screening pigs to determine those more likely to produce larger litters, and/or those less likely to produce larger litters, which method comprises the steps:
 (i) obtaining a sample of genomic DNA from a pig;
 (ii) hybridising the genomic DNA from (i) with one or more suitable primers;
 (iii) carrying out one or more PCR cycles using the hybridised nucleic acid from (ii); and
 (iv) analysing the length of the PCR product obtained in (iii).

Suitably, the methods of the present invention are carried out using reagents and instructions presented in the form of a kit.

Thus, in a third aspect, the present invention provides a kit for screening pigs to determine those more likely to produce larger litters, and/or those less likely to produce larger litters, by determining whether the pigs carry the FSH-β mutation. In one mode this comprises one or more reagents or materials capable of identifying FSH β-subunit alleles in a sample of pig genomic DNA.

In one embodiment of this aspect of the invention the kit will comprise reagents or materials capable of identifying alleles associated with DNA markers linked to the FSH β-subunit gene, eg. a microsatellite marker. Such a kit would most preferably comprise one or more DNA primers optionally together with standard PCR reagents. In another embodiment, the kit will comprise antibodies which distinguish between FSH β with or without the retroposon.

Finally, the skilled person will realise that the methods and kits described herein can be used in conjunction with other already described methods and kits to screen pigs to determine those more likely to produce larger litters (or those less likely to). An example of such other methods and kits are those described in WO92/18651 and WO96/41892 (both of which are hereby incorporated by reference). It would, of course, be possible to produce combined kits which could be used to screen pig DNA using all these methods.

Thus, in a further aspect, the present invention provides a method for screening pigs to determine those more likely to produce larger litters, and/or those less likely to produce larger litters, which method comprises the steps:
 (i) obtaining a sample of genomic DNA from a pig;
 (ii) analysing the genomic DNA obtained in step (i) to determine which FSH β-subunit gene allele(s) is/are present; and
 (iii) analysing the genomic DNA obtained in step (i) to determine which allele(s) of at least one other gene linked to litter size in pigs is/are present.

In preferred embodiments of this aspect of the invention the at least one other gene is the ESR gene, as described in WO-A-9218651 or the OPN gene as described in WO96/41892.

In a final aspect the present invention provides a kit for screening pigs to determine those more likely to produce larger litters, and/or those less likely to produce larger litters, which comprises one or more reagents or materials capable of identifying FSH β-subunit gene alleles in a sample of pig genomic DNA, together with one or more reagents or materials capable of identifying alleles of at least one other gene linked to litter size in pigs in a sample of pig genomic DNA.

Preferred features of each aspect of the invention are applicable to each other aspect *Mutatis mutandis*.

The invention will now be described with reference to the following examples, which should in no way be construed as limiting the invention

EXAMPLE 1

Materials and Methods

Blood and Ear Tissues Sample

Blood was collected from porcine vena cava anterior. ACD was used as antiagglutinator, and samples stored at −20° C. Ear tissues were stored at −20° C. with 70% ethanol.

PCR Primers

Design of primers was according to published FSH β gene sequence (T. Hirai et al., 1990) as follows:

```
forward:  5'CCTTTAAGACAGTCAATGC 3'   (SEQ ID NO:3);

and reverse:  5'ACTGGTCTATTCATCCTCTC 3'  (SEQ ID NO:4)
```

Southern Blotting

Genomic DNA isolation according to Molecular cloning (J. Sambrook et al. Molecular cloning second edition, Cold Spring Harbour Laboratory Press, New York (1989), incorporated herein by reference). Digest a 5 ug DNA sample with BamHI. Transfer DNA to Nylon membrane from gel after electrophoresis. Prehybridize at 42° C. for 3 hours with 5XSSC, 0.02% SDS, 1% blocking reagent, 0.1% N lauroylsarcosine, then hybridize at 68° C. for 16–24 hours with 5XSSC, 0.02% SDS, 1% blocking reagent, 0.1% N lauroylsarcosine and digoxigenin labelled FSH β subunit cDNA probe. Treat the membrane according to DIG protocol after hybridization.

Polymerase Chain Reaction 100 ng genomic DNA is used as template. The PCR protocol is that 25 μl PCR mixture contains 10 mmol/L TrisCl pH 8.0, 50 mmol/L KCl, 1 mmol/L MgCl, 0.01% gelatin, 200 μmol/L dNTP, 1.0 μmol/L primers, 2U Taq DNA polymerase. The mixture was incubated on Gene Amp PCR system 9600 with a programme of denaturation at 94° C. for 2 min, followed by 30 cycles of 94° C. for 30 sec, 55° C. for 30 sec, 72° C. for 30 sec, and final holding at 72° C. for 7 min. The PCR products are identified by agarose gel electrophoresis.

Sequencing

The PCR product was cloned into pGEM-3Zf(+), prepare plasmid template for sequencing by ABI 370A Sequencer.

Genotyping

Genotyping animals according to PCR polymorphism. Three genotype AA, AB, BB represents each for animal with 0.5 kb PCR band, 0.5 kb, 0.2 kb bands, and 0.2 kb PCR band.

Results and Discussion

Variations of the 5' Flanking Region of FSH β Subunit Gene Among Pig Breeds

Analysis of 5' regulating region will be helpful to understand the gene expression. As we know, high concentrations of FSH and LH can induce estrus synchronization and superovulation. Some experimental results show that there is larger concentration of FSH in circulation blood of Meishan gilts and boars (Jiao et al, *Acta Veterinaria et Zootechnica*, 23(3):202–206 (1992); Wise et al, *Biol. Reprod.*, 54:146–153 (1996)) than European breeds. We want to certify whether changes in FSH concentration results from the diversity of 5' flanking region between breeds. Our findings indicated no difference exists in potential CRE, AP1, AP2 responsive element and CAT box, TATA box. On the other hand, a traversion of C→A in −439 base position appears between Chinese pig breeds and western pig breeds. Around −360 base position, microsatellite site of (AT) n repeats was found with two alleles (AT)7, (AT) 11, (Zhao et al., Proceedings of 8th National Symposium on Animal genetics and Breeding, Wuxi: Chinese Agricultural Technology Press, pp51–53 (1995)). None of the above variations appear to be responsible for difference of FSH concentration between Meishan or Erhualian and other breeds.

RFLPs Analysis of FSH β Subunit Gene

We used the porcine FSH β subunit cDNA to detect polymorphism of FSH β subunit genomic gene. Endonuclease included BamHI, EcoRI, HindIII. A significant polymorphism was obtained when using BamHI where prolific Taihu pig (Meishan, Erhualian) has consistent 3.0 kb hybridization band. The other pig breeds (Landrace, Yorkshire, Chinese Minipig) contrarily with 3.0 kb and 3.2 kb or 3.5 kb hybridization band (Zhao et al., *Acta Veterinaria* et *Zootechnica Sinica* (1997)). This phenomenon is caused by an insertion with a BamHII recognition site in FSH β gene structural region (Zhao et al, unpublished). This polymorphism can be used as a DNA marker to analyze whether FSH β gene does contribution to prolificacy of Meishan.

Genotyping Animals by PCR

In 1995 we discovered a PCR length polymorphism of FSH β structural gene which caused by an insertion (Zhao et al., (1995), supra). Further precise location of this insertion has been done in our group (Zhao et al., unpublished). This insertion contains 292 bases with a polyA which can't be found in the published FSH β gene sequence. But the significance of insertion or deletion remains to be unclear. According to the results described herein, using primers designed to genotype animals, genotypes were classified by PCR product into three kinds, two homozygotes AA, BB each with 0.5 kb or 0.2 kb band, AB heterozygote with 0.5 kb and 0.2 kb bands. A large scale analysis has been made with results of all breeds being in gene balance. 100% AA animals for Chinese pig breeds. Contrarily, BB genotype is prevalent in Yorkshire, Landrace and Duroc breeds.

TABLE 1

Results of genotyping among pig breeds in FSH β locus

| Pig breed | CDG | | | | GF | | CGF | | | TGF | | |
|---|---|---|---|---|---|---|---|---|---|---|---|---|
| | AA | AB | BB | | A | B | AA | AB | BB | AA | AB | BB |
| Erhualian | 50 | 0 | 0 | 50 | 1.00 | 0 | 1.00 | 0 | 0 | 1.00 | 0 | 0 |
| Chinese | 70 | 0 | 0 | 70 | 1.00 | 0 | 1.00 | 0 | 0 | 1.00 | 0 | 0 |

TABLE 1-continued

Results of genotyping among pig breeds in FSH β locus

| Pig breed | CDG | | | GF | | CGF | | | TGF | | |
|---|---|---|---|---|---|---|---|---|---|---|---|
| | AA | AB | BB | A | B | AA | AB | BB | AA | AB | BB |
| minipig | | | | | | | | | | | |
| Landrace | 4 | 36 | 82 | 122 | 0.1803 | 0.8196 | 0.0328 | 0.2950 | 0.6721 | 0.0325 | 0.2955 | 0.6717 |
| Yorkshire | 3 | 29 | 157 | 189 | 0.0926 | 0.9074 | 0.015 | 0.1534 | 0.8307 | 0.0085 | 0.1681 | 0.8234 |

CDG = "Checked distribution of genotype" (number of individuals by genotype)
GF = "Gene frequency"
CGF = "Checked gene frequency"
TFG = "Theoretic genotype frequency"

FSH β Subunit Genotype and Litter Size in Swine

Litter size records of 289 sows of Landrace, Yorkshire were collected and used to estimate the gene effect on reproduction. Statistical data suggested that the BB homozygote females produced on average 2.53 piglets more than did AA sows for total number born (TNB) of the first parity and 2.12 for number born alive. To all parities, more 1.5 more piglets per litter are produced by BB sows than AA females. No negative effect be concluded for BB sows on body weight at birth and 20 days of piglets. FSH β gene may be associated with major gene of reproduction in these populations.

Conclusions

A candidate gene approach has been employed to locate a major gene for QTL. By this method, Rothschild and his colleagues put forward that the estrogen receptor gene is closely associated with a major gene of litter size in large white population (Rothschild et al., *P.N.A.S USA*, 93:201–205 (1996)). The present inventors have looked at the FSH β gene as a candidate gene to analyze its effect on pig litter size. Significant variation was found between Taihu pig and other breeds. A PCR program was created to genotype sows with records of litter size. Further results indicate the FSH β subunit locus may be linked to a major gene of litter size in Yorkshire and Landrace populations.

EXAMPLE 2

Analysis of Samples From 1000 Sows

Samples have been collected over 1000 sows', and FSH β genotyping was performed, according to the methodologies described in Example 1. All the reproduction performance of these sows have been recorded and computed with a linear model to estimate the genetic effects. The results are summarized in Table 2. Again it can be seen that the B allele, ie where the retroposon is absent, is associated with increased litter size.

TABLE 2

Effect of the FSH Genotypes on Reproductive Traits

| FSH Genotype | Parity 1 | | | Parity 2 | | | Parity 3 | | | Parity 4 | | |
|---|---|---|---|---|---|---|---|---|---|---|---|---|
| | N | TNB | NBA | N | TNB | NBA | N | TNB | NBA | N | TNB | NBA |
| AA | 187 | 8.13 | 7.62 | 93 | 8.92 | 8.33 | 71 | 9.12 | 8.42 | 48 | 9.18 | 8.48 |
| AB | 371 | 9.88 | 9.28 | 230 | 10.62 | 10.27 | 122 | 11.58 | 10.83 | 92 | 11.92 | 10.65 |
| BB | 532 | 10.67 | 9.62 | 414 | 11.54 | 11.12 | 283 | 12.13 | 11.26 | 121 | 12.17 | 11.38 |
| a | | 1.27 | 1.00 | | 1.31 | 1.39 | | 1.50 | 1.42 | | 1.51 | 1.45 |
| d | | 0.48 | 0.66 | | 0.39 | 0.55 | | 0.95 | 0.79 | | 0.95 | 0.72 |
| D | | 0.38 | 0.66 | | 0.30 | 0.39 | | 0.63 | 0.56 | | 0.61 | 0.50 | a = (BB − AA)/2
d = (AB − (AA − BB)/2
D = d/a
N = no. of pigs;
TNB = total number born in litter;
NBA = number born alive

What is claimed is:

1. A method for screening pigs to determine those more or less likely to produce larger litters, which method comprises determining which FSH β-subunit allele(s) is/are present in the genome of individual pigs, wherein the determination of FSH β-subunit allele(s) comprises determining the presence of at least one allele associated with at least one DNA marker linked either directly or indirectly to the FSH β-subunit gene, wherein the DNA marker is a retroposon, and wherein the presence of certain alleles indicates an increased likelihood of producing a larger litter.

2. A method for screening pigs to determine those more or less likely to produce larger litters, which method comprises the steps:

(i) obtaining a sample of pig nucleic acid; and (ii) analyzing the nucleic acid obtained in (i) to determine which FSH β-subunit allele(s) is/are present, wherein the determination of FSH β-subunit allele(s) comprises determining the presence of at least one allele associated with at least one DNA marker linked either directly or indirectly to the FSH β-subunit gene, wherein the DNA marker is a retroposon, and wherein the presence of certain alleles indicates an increased likelihood of producing a larger litter.

3. The method of claim 1 or 2, wherein the retroposon has the sequence of SEQ ID NO:1.

* * * * *